United States Patent [19]

Saotome et al.

[11] 3,953,504

[45] Apr. 27, 1976

[54] RACEMIZATION OF OPTICALLY ACTIVE TARTARIC ACID

[75] Inventors: Minoru Saotome, Koriyama; Yoshikazu Yamamoto, Ikeda; Nobuo Watani, Kyoto; Ryuichi Kayama, Koriyama, all of Japan

[73] Assignees: Nippon Peroxide Co., Ltd., Tokyo; Showa Chemical Co., Ltd., both of Japan

[22] Filed: Mar. 18, 1975

[21] Appl. No.: 559,416

[52] U.S. Cl. .............................................. 260/536
[51] Int. Cl.² ....................................... C07C 59/14
[58] Field of Search ................................... 260/536

[56] References Cited

UNITED STATES PATENTS 3,405,159   10/1968   Krieger .............................. 260/536

*Primary Examiner*—Anton H. Sutto
*Assistant Examiner*—P. J. Killos
*Attorney, Agent, or Firm*—Oblon, Fisher, Spivak, McClelland & Maier

[57] ABSTRACT

An optically active enantiomer of tartaric acid or a salt thereof is racemized by mixing meso-tartaric acid or a salt thereof with a solution of an optically active enantiomer of tartaric acid or a salt thereof in a molar ratio of 0.2 – 0.5 and thereafter heating the mixture.

7 Claims, No Drawings

RACEMIZATION OF OPTICALLY ACTIVE TARTARIC ACID

BACKGROUND OF THE INVENTION

1. Field of the Invention

The present invention relates to the racemization of optically active tartaric acid.

2. Description of the Prior Art

Tartaric acid exists as the optically active enantiomers, L-tartaric acid and D-tartaric acid, as well as racemic DL-tartaric acid and meso-tartaric acid. Naturally occurring tartaric acid is mainly L-tartaric acid.

L-tartaric acid is produced as a by-product from argol in the manufacture of the juice from the grape (wine). Further, L-tartaric acid is used as a food additive in refreshing drinks.

The tartaric acid produced by synthetic processes is DL-tartaric acid, and accordingly when L-tartaric acid is separated from the racemic mixture by optical resolution, the same amount of D-tartaric acid is produced as a by-product. D-tartaric acid is not approved as a food additive, and accordingly D-tartaric acid is of little value. In order to increase the value of D-tartaric acid, it is necessary to racemize the D-tartaric acid. It has been known to racemize optically active tartaric acid by heating the isomer in an alkaline solution or in an aqueous solution of the optically active tartaric acid. In this method, a large amount of meso-tartaric acid is produced as a by-product. In fact, the method is known as a method of manufacturing meso-tartaric acid. Of course, the formation of mesotartaric acid causes a decrease in the yield of DL-tartaric acid. Consequently, in order to increase the yield of DL-tartaric acid, it is necessary to prevent as much as possible the formation of meso-tartaric acid. A need, therefore, continues to exist for a method of racemizing D-tartaric acid without the formation of meso-tartaric acid as a by-product.

SUMMARY OF THE INVENTION

Accordingly, one object of the present invention is to provide a method of racemizing optically active tartaric acid in high yield to DL-tartaric acid.

Briefly, this object and other objects of the invention, as hereinafter will become more readily apparent, can be attained in the racemization of an optically active tartaric acid by adding meso-tartaric acid or a salt thereof to a solution of an optically active enantiomer of tartaric acid, and heating the mixture.

DETAILED DESCRIPTION OF THE PREFERRED EMBODIMENTS

The racemization of an optically active enantiomer of tartaric acid has been studied in attempts to increase the yield of product DL-tartaric acid. The equilibrium relationships of meso-tartaric acid, the optically active tartaric acids, and DL-tartaric acid were studied and the equilibrium concentration of the acids is in the range of industrial application. The maximum equilibrium amount of meso-tartaric acid is limited, so that the amount of the newly formed meso-tartaric acid can be decreased commensurate with the amount of meso-tartaric acid added before the equilibrium reaction occurs. Consequently, the yield of DL-tartaric acid increases depending upon the amount of meso-tartaric acid added. The heart of the present invention for the racemization of an optically active tartaric acid resides in the addition of meso-tartaric acid or a salt thereof to a reaction mixture containing an optically active tartaric acid such that the amount of meso-tartaric acid formed is decreased.

In the practical aspects of the invention, meso-tartaric acid is added to a solution of D-tartaric acid containing a catalyst of an alkaline compound such as sodium hydroxide. Subsequently, the solution is heated to racemize the D-tartaric acid. The yield of racemate increases as a function of increasing concentration of the alkaline catalyst. The amount of the alkaline catalyst can be decreased and the reaction time can be shortened without a decrease in the yield of reaction product at high temperature under high pressure. The rate of racemization is substantially the same when either sodium hydroxide or potassium hydroxide is used as the alkaline catalyst. It is unnecessary to separately prepare meso-tartaric acid because the by-product meso-tartaric acid produced in prior racemization reactions can be recycled to subsequent racemization reactions. Previously, it has been difficult to prevent the formation of large amounts of by-product meso-tartaric acid, and consequently industrial application of the racemization reaction has been limited.

The following is a preferred embodiment of the system for producing L-tartaric acid from maleic anhydride. Maleic anhydride is epoxidated by a hydrogen peroxide solution in the presence of a catalyst of sodium tungstate, and the product is hydrolyzed under refluxing conditions to produce DL-tartaric acid. The resulting solution contains tartaric acid (more than 80% DL-tartaric acid), and is cooled to precipitate DL-tartaric acid as a crystalline material. The mother liquor is then neutralized with an alkali such as ammonia, sodium hydroxide, or potassium hydroxide, to form the mono-alkali salt of DL-tartaric acid as a second batch of crystals. The crystalline DL-tartaric acid and the crystals of the alkali salt of DL-tartaric acid are mixed and dissolved in water with an alkali such as ammonia, sodium hydroxide, or potassium hydroxide to form DL-Pasteur salt (ammonium sodium tartrate) or DL-Rochelle salt (potassium sodium tartrate). Thereafter, the solution is cooled and is fed into an optical resolution separator together with a slurry of seed crystals of a D-tartrate such as D-Pasteur salt, D-Rochelle salt, or the like to promote the precipitation of D-tartrate. In a second optical resolution separator, an L-tartrate material such as L-Pasteur salt or L-Rochelle salt is added to the mother liquor to precipitate an L-tartrate such as the L-Pasteur salt, the L-Rochelle salt, or the like. The D-tartrate is then racemized by adding meso-tartaric acid or a salt thereof and an alkali to the D-tartrate in accordance with the above-mentioned process. In the racemization reaction, meso-tartaric acid or a salt thereof is added in amounts spanning a molar ratio of 0.2 – 0.5, preferably 0.3 – 0.35 to total tartaric acid. Also, an alkali is added in amounts spanning a molar ratio of 0.1 – 10, preferably 0.4 – 0.8 of free alkali to total tartaric acid. The racemization temperature is usually 80° – 200°C, preferably 90° – 170°C, especially 120° – 140°C. An acidic component can be added to the reaction mixture to form the mono-alkali salt of tartaric acid. The mono-alkali salt of DL-tartaric acid is precipitated and the DL-tartrate is recycled to the optical resolution separator. The mother liquor contains meso-tartrate and DL-tartrate (20 – 30% of meso-tartrate) and is recycled to the racemization process, as stated above, as a source of meso-tartaric acid.

In the crystallization of the mono-alkali salt of DL-tartaric acid, the DL-tartaric acid solution prepared in the first step can be added as an acidic component. In accordance with the present process, almost all of the maleic acid or anhydride can be converted to L-tartaric acid or a salt thereof by the racemization reaction and the recycling process. Accordingly, the amount of meso-tartaric acid formed can be decreased significantly, and a substantial amount of the synthetic DL-tartaric acid can be converted to valuable L-tartaric acid thereby achieving a successful industrial route for the synthesis of L-tartaric acid.

Having generally described the invention, a further understanding can be obtained by reference to certain specific Examples which are provided herein for purposes of illustration only and are not intended to be limiting unless otherwise specified.

REFERENCE EXAMPLE 1

Into a test tube equipped with a reflux condenser were charged 4.86 g of D-tartaric acid, 7.78 g of sodium hydroxide and 10.6 g of water. The mixture was heated at 116°C in an oil bath for 8 hours under reflux. Analysis of the resulting reaction mixture gave 0.11 g of unreacted D-tartaric acid, 2.45 g of DL-tartaric acid and 1.79 g of meso-tartaric acid. The conversion of D-tartaric acid to DL-tartaric acid was 50.4%.

EXAMPLE 1

Into a test tube were charged 3.40 g of D-tartaric acid, 1.46 g of meso-tartaric acid, 7.78 g of sodium hydroxide and 10.6 g of water. Following the process of Reference Example 1, the racemization of D-tartaric acid was conducted and the reaction mixture was analyzed to give 0.08 g of unreacted D-tartaric acid, 2.62 g of DL-tartaric acid and 1.72 g of meso-tartaric acid. The conversion of D-tartaric acid to DL-tartaric acid was 77.1%.

EXAMPLE 2

Into a test tube was charged 12.3 ml of a filtrate prepared by separating DL-tartaric acid from the solution of Example 1 which contained 0.10 g of D-tartaric acid, 0.07 g of DL-tartaric acid, 1.61 g of meso-tartaric acid and 11.8 g of water. Also, 3.65 g of D-tartaric acid and 8.69 g of sodium hydroxide were charged to the solution. The racemization of D-tartaric acid was then conducted by the procedure of Reference 1, and the reaction mixture was analyzed to give 0.09 g of D-tartaric acid, 2.88 g of DL-tartaric acid and 1.81 g of meso-tartaric acid. The conversion of D-tartaric acid to DL-tartaric acid was 74.9%.

EXAMPLE 3

A sealed tube containing 3.16 g of D-tartaric acid, 1.70 g of mesotartaric acid, 3.36 g of sodium hydroxide and 11.54 g of water was heated in an oil bath at 130°C for 5 hours. The resulting reaction mixture was analyzed to give 0.21 g of D-tartaric acid, 2.70 g of DL-tartaric acid and 1.68 g of meso-tartaric acid. The conversion of D-tartaric acid to DL-tartaric acid was 85.4%.

EXAMPLE 4

Into a 5-liter stainless steel reactor, 676 g of maleic anhydride, 720 ml of 35% hydrogen peroxide and 2 liters of water were charged, and 6.6 g of sodium tungstate ($Na_2WO_4 \cdot 2H_2O$) was added. Epoxidation was conducted at 70°C for 16 hours, and then the mixture was refluxed for 3 hours to hydrolyze the epoxide. The reaction product was cooled and the mother liquor was separated by a centrifugal separator whereby 615 g of crystalline DL-tartaric acid was obtained. A 220 ml amount of 28% aqueous ammonia was added to the mother liquor and 180 g of mono-ammonium DL-tartrate were obtained as a second batch of crystals. The crystals of DL-tartaric acid and of mono-ammonium DL-tartrate were mixed and the mixture was dissolved with heating in a mixture of 1582 ml of water, 292 ml of 28% aqueous ammonia, and 207 g of sodium hydroxide. The solution was cooled and kept at 40°C. The solution was then cooled to 16°C and fed from the top of a tower type optical resolution separator together with a slurry of seed crystals of L-Pasteur salt. The temperature was maintained at 16°C and the optical resolution of L-Pasteur salt was conducted. In a second optical resolution separator, D-Pasteur salt was separated. In an autoclave, 337 g of D-Pasteur salt was mixed with 200 g of sodium hydroxide, 200 ml of water and 50 g of meso-tartaric acid and the racemization was performed at 130°C for 3 hours. The preparation of DL-tartaric acid was repeated whereby 618 g of DL-tartaric acid were obtained as the first batch of crystals. The racemization reaction mixture was added to the first crystals of DL-tartaric acid and 998 g of mono-sodium DL-tartrate were obtained. The mono-sodium DL-tartrate was added to 179 g of the second batch of crystals of mono-ammonium DL-tartrate from the second reaction, and the mixture was dissolved in a mixture of 43 g of sodium hydroxide and 414 ml of 28% aqueous ammonia. The solution was cooled whereby 1,650 g of DL-Pasteur salt were obtained. The Pasteur salt was acidified with sulfuric acid and 850 g of L-tartaric acid were obtained.

Having now fully described the invention, it will be apparent to one of ordinary skill in the art that may changes and modifications can be made thereto without departing from the spirit or scope of the invention as set forth herein.

What is claimed as new and intended to be secured by letters patent is:

1. A process for the racemization of optically active tartaric acid or a salt thereof, which comprises:
    mixing meso-tartaric acid or a salt thereof with a solution of an optically active enantiomer of tartaric acid or a salt thereof in a molar ratio of 0.2 – 0.5, and thereafter heating the mixture.

2. The process of claim 1, wherein an alkali is added to said mixture in a molar ratio of 0.1 – 10 of the free alkali based on the total amount of tartaric acid, and the mixture is heated at 80° – 200°C.

3. The process of claim 2, wherein the mother liquor containing meso-tartaric acid and prepared by separating DL-tartaric acid from the racemization mixture by addition of an acidic material, is recycled and then added to a solution of an optically active enantiomer of tartaric acid or a salt thereof.

4. The process of claim 3, wherein said racemization of an optically active enantiomer of tartaric acid or a salt thereof is performed at 80° – 200°C by adding meso-tartaric acid or a salt thereof to said enantiomer at a molar ratio of 0.2 – 0.5 and a free alkali at a molar ratio of 0.1 – 10.

5. The process of claim 3, wherein said racemization of an optically active enantiomer of tartaric acid or a salt thereof is performed at 120° – 140°C by adding meso-tartaric acid or a salt thereof to said enantiomer at a molar ratio of 0.3 – 0.35 and a free alkali at a molar ratio of 0.4 – 0.8.

6. A process for producing L-tartaric acid or a salt thereof, which comprises:

forming DL-tartaric acid by reacting maleic acid or anhydride with a peroxide and hydrolyzing the resulting oxide product; optically resolving DL-tartaric acid into L-tartaric acid and D-tartaric acid, or the respective salts thereof; racemizing said D-tartaric acid or salt thereof by mixing meso-tartaric acid or a salt thereof with said D-tartaric acid or salt thereof; separating DL-tartaric acid or salt thereof from a mother liquor containing meso-tartaric acid or a salt thereof; recycling the mother liquor containing said meos-tartrate to the racemization step; and recycling said DL-tartrate to the optical resolution step.

7. The process of claim 6, wherein alkali is added to the mixture of D-tartaric acid or salt thereof and meso-tartrate in a molar ratio of 0.1 – 10 of free alkali to the total amount of tartaric acid, and the mixture is heated to 80° – 200°C.

* * * * *